United States Patent
Gering

(10) Patent No.: US 7,831,077 B2
(45) Date of Patent: Nov. 9, 2010

(54) METHOD AND APPARATUS FOR GENERATING AN IMAGE USING MRI AND PHOTOGRAPHY

(75) Inventor: David T. Gering, Waukesha, WI (US)

(73) Assignee: General Electric Co., Schenectady, NY (US)

( * ) Notice: Subject to any disclaimer, the term of this patent is extended or adjusted under 35 U.S.C. 154(b) by 900 days.

(21) Appl. No.: 11/683,244

(22) Filed: Mar. 7, 2007

(65) Prior Publication Data

US 2008/0219538 A1    Sep. 11, 2008

(51) Int. Cl.
*G06K 9/00* (2006.01)
(52) U.S. Cl. .................. 382/128; 382/130; 382/131; 382/132; 382/154
(58) Field of Classification Search .............. 382/128, 382/131, 132, 154, 285
See application file for complete search history.

(56) References Cited

U.S. PATENT DOCUMENTS 5,970,499 A * 10/1999 Smith et al. .................. 1/1

OTHER PUBLICATIONS

Wellmer, J., Von Oerzen, J., Schaller, C., Urbach, H., Konig, R., Widman, G., Van Roost, D., and Elger, C. E.. "Digital Photography and 3D MRI-based Multimodal Imaging for Individual Planning of Resective Neocortical Epilepsy Surgery." Epilepsia. 2002, p. 1543-1550, vol. 43, No. 12.

"Project on Image Guided Surgery: A Collaboration Between the MIT AI Lab and Brigham and Woman's Surgical Planning Laboratory."Image Guided Surgery. http://groups.csail.mit.edu/vision/medical-vision/surgery/surgical$_{13}$ navigation.html, p. 1-5.

* cited by examiner

*Primary Examiner*—Tom Y Lu

(57) ABSTRACT

A method for generating an image of a region of interest of a subject includes obtaining a set of magnetic resonance (MR) data for the region of interest. In addition, photographic data for at least one surface of the region of interest is obtained, for example, from a database or by using a camera for photographing the region of interest. An image is generated by using the set of MR data to generate a depiction of at least one structure of the region of interest and by using the photographic data to generate a depiction of at least one surface of the region of interest.

23 Claims, 4 Drawing Sheets

METHOD AND APPARATUS FOR GENERATING AN IMAGE USING MRI AND PHOTOGRAPHY

TECHNICAL FIELD

The present invention relates generally to magnetic resonance imaging (MRI) systems and in particular, to a method and apparatus for generating an image based on MRI data and photographic data.

BACKGROUND

Magnetic resonance imaging (MRI) is a medical imaging modality that can create pictures of the inside of a human body without using x-rays or other ionizing radiation. MRI data may be acquired as three-dimensional (3-D) data-sets and displayed as two-dimensional (2-D) images corresponding to individual slices through the 3-D data-set. Alternatively, a 3-D MRI data-set may be displayed as a 2-D image using a format that seeks to represent objects of interest in the data-set from the perspective of a hypothetical external observer. Examples of methods for generating a 2-D image from a 3-D MRI data set include "volume-rendering" and "surface-rendering" techniques.

In volume-rendering techniques, each "voxel" (or volume element) of a 3-D data-set is assigned a color and opacity based on its image intensity. Rays are then cast from a virtual camera at the location of a theoretical observer into the 3-D image data, with each ray generating a single pixel in the resultant 2-D image. The color produced by the ray at the resultant pixel is determined from the color and opacity values of the voxels encountered along its trace.

In surface-rendering techniques, the 3-D image data is first "segmented", i.e., each voxel in the data-set is assigned a label corresponding to a predefined tissue type. Then, a polygonal mesh is wrapped around the segmented tissue structures to form surface models for the structures. Typically, each surface is displayed using a single color and opacity that are assigned on the basis of the corresponding tissue type. Alternatively, a color for a surface may be determined based on measured surface properties such as curvature and thickness.

For many clinical applications, depicting a 3-D MRI data-set using such known techniques is sufficient. However, advanced applications such as MRI-guided surgery or MRI-assisted endoscopy may benefit from more sophisticated image display techniques. It may be useful to provide improved renderings of surfaces (e.g., organ surfaces, skin surfaces) in such applications to aid in, for example, surgical planning. Accordingly, it would be desirable to provide a method and apparatus for providing more accurate surface renderings for MRI images. In particular, it would be desirable to provide a method and apparatus for combining photographic image data with 3-D MRI data.

BRIEF DESCRIPTION OF THE INVENTION

In accordance with an embodiment, a method for generating an image of a region of interest of a subject includes obtaining a set of magnetic resonance (MR) data for the region of interest, obtaining photographic data for at least one surface of the region of interest and generating an image using the set of MR data to generate a depiction of at least one structure of the region of interest and using the photographic data to generate a depiction of at least one surface of the region of interest.

In accordance with another embodiment, a computer readable medium having computer executable instructions for performing a method for generating an image of a region of interest of a subject includes program code for receiving a set of magnetic resonance (MR) data for the region of interest, program code for receiving photographic, data for at least one surface of the region of interest and program code for generating an image using the set of MR data to generate a depiction of at least one structure of the region of interest and using the photographic data to generate a depiction of at least one surface of the region of interest In accordance with another embodiment, an apparatus for generating an image of a region of interest of a subject includes a camera configured to obtain photographic data for at least one surface of the region of interest, a magnetic resonance imaging assembly configured to obtain a set of magnetic resonance (MR) data for the region of interest and an image processor coupled to the camera and the magnetic resonance imaging assembly, the image processor configured to generate an image using the set of MR data to generate a depiction of at least one structure of the region of interest and using the photographic data to generate a depiction of at least one surface of the region of interest.

In accordance with yet another embodiment, an apparatus for generating an image of a region of interest of a subject includes a database comprising photographic data, a magnetic resonance imaging assembly configured to obtain a set of magnetic resonance (MR) data for the region of interest and an image processor coupled to the database and the magnetic resonance imaging assembly, the image processor configured to generate an image using the set of MR data to generate a depiction of at least one structure of the region of interest and using a selected set of photographic data from the database to generate a depiction of at least one surface of the region of interest.

BRIEF DESCRIPTION OF THE DRAWINGS

Embodiments are illustrated by way of example and not limitation in the figures of the accompanying drawings, in which like reference numerals indicate corresponding, analogous or similar elements, and in which.

DETAILED DESCRIPTION

In the following detailed description, numerous specific details are set forth in order to provide a thorough understanding of embodiments. However it will be understood by those of ordinary skill in the art that the embodiments may be practiced without these specific details. In other instances, well-known methods, procedures, components and circuits have not been described in detail so as not to obscure the embodiments.

MRI data and photographic data may be combined to generate 2-D images that accurately depict both the internal and external properties of a patient's anatomy. The MRI data provides information about the internal anatomical structures and the photographic data provides information about the surfaces. Such 2-D representations are particularly desirable for clinical applications that require reference to anatomical landmarks on the patient's skin or on the surface of an organ or tissue, while simultaneously visualizing internal structures. Photographic data of a patient may be obtained during an MR imaging session or generic photographic data may be used. The photographic data may be used to depict the surfaces of organs or tissues or the patient's skin. The use of photographic data to enhance the depiction of surfaces in 2-D representations of a 3-D MR image data-set may increase the realism and accuracy of the images. These more realistic representations may facilitate MRI-guided surgical interventions or MRI-assisted endoscopic procedures by, for example, displaying anatomical landmarks from the skin and/or organ or tissue surfaces simultaneously with the internal structures depicted using the MRI data.

Figure 1:
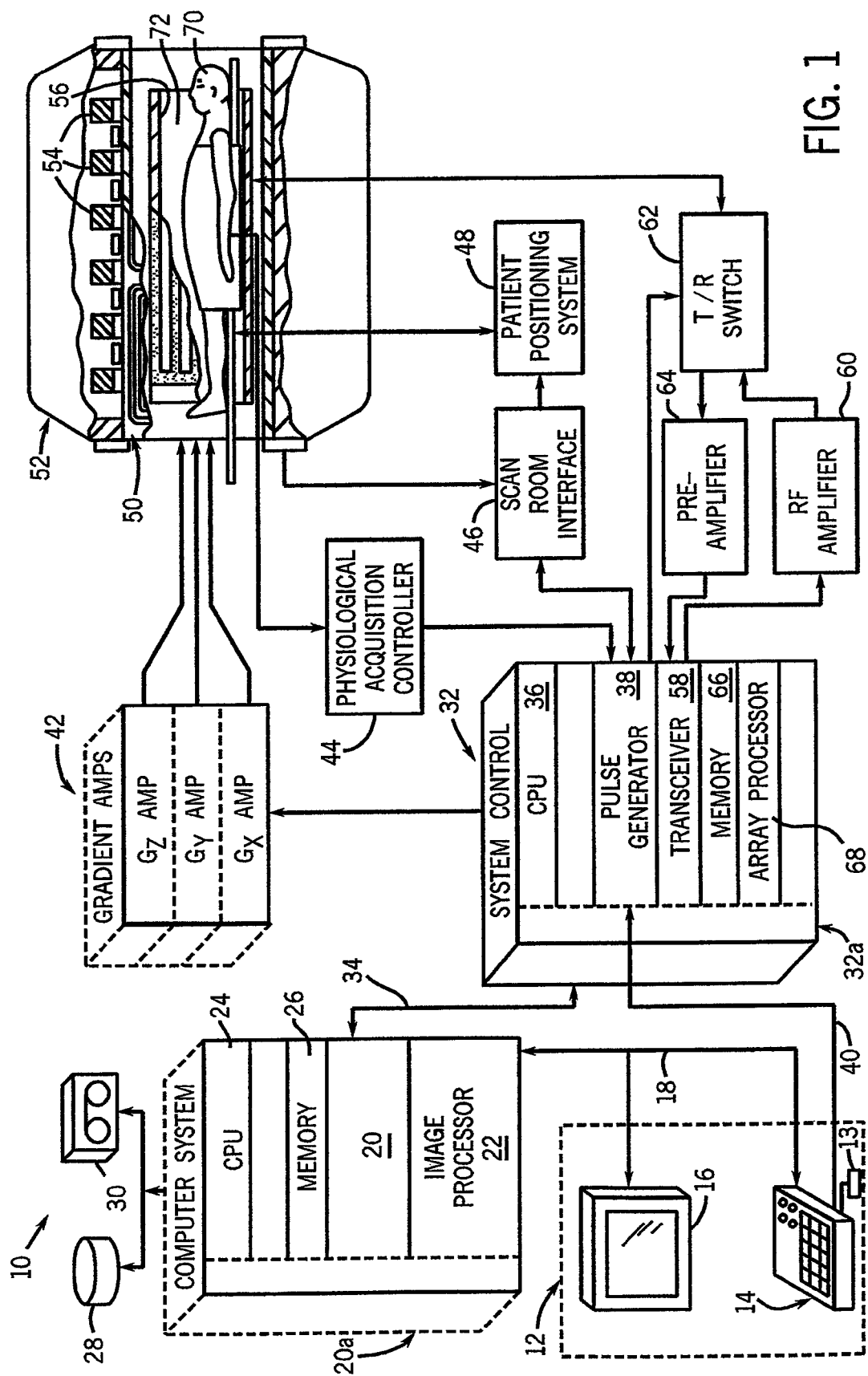
FIG. 1 is a schematic block diagram of a magnetic resonance imaging system in accordance with an embodiment.

FIG. 1 is a schematic block diagram of a magnetic resonance imaging system in accordance with an embodiment. The operation of MRI system 10 is controlled from an operator console 12 that includes a keyboard or other input device 13, a control panel 14 and a display 16. The console 12 communicates through a link 18 with a computer system 20 and provides an interface for an operator to prescribe MRI scans, display the resultant images, perform image processing on the images, and archive data and images. The computer system 20 includes a number of modules that communicate with each other through electrical and/or data connections, for example such as are provided by using a backplane 20a. Data connections may be direct wired links or may be fiber optic connections or wireless communication links or the like. The modules of computer system 20 may include an image processor module 22, a CPU module 24 and a memory module 26 that may include a frame buffer for storing image data arrays. In an alternative embodiment, the image processor module 22 may be replaced by image processing functionality on the CPU module 24. The computer system 20 is linked to archival media devices, such as disk storage 28 and tape drive 30, for storage of image data and programs and communicates with a separate system control computer 32 through a link 34. Archival media include, but are not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which may be used to store the desired instructions and which can be accessed by computer system 20, including by internet or other computer network forms of access. The input device 13 can include a mouse, joystick, keyboard, track ball, touch activated screen, light wand, voice control, or any similar or equivalent input device, and may be used for interactive geometry prescription.

The system control computer 32 includes a set of modules in communication with each other via electrical and/or data connections 32a. Data connections 32a may be direct wired links or may be fiber optic connections or wireless communication links or the like. In alternative embodiments, the modules of computer system 20 and system control computer 32 may be implemented on the same computer systems or a plurality of computer systems. The modules of system control computer 32 include a CPU module 36 and a pulse generator module 38 that connects to the operator console 12 through a communications link 40. The pulse generator module 38 may alternatively be integrated into the scanner equipment (e.g., magnet assembly 52). It is through link 40 that the system control computer 32 receives commands from the operator to indicate the scan sequence that is to be performed. The pulse generator module 38 operates the system components that play out (i.e., perform) the desired pulse sequence and produces data called RF waveforms which control the timing, strength and shape of the RF pulses to be used and the timing and length of the data acquisition window. The pulse generator module 38 connects to a gradient amplifier system 42 and produces data called gradient waveforms which control the timing and shape of the gradient pulses that are to be used during the scan. The pulse generator module 38 may also receive patient data from a physiological acquisition controller 44 that receives signals from a number of different sensors connected to the patient, such as ECG signals from electrodes attached to the patient. The pulse generator module 38 connects to a scan room interface circuit 46 that receives signals from various sensors associated with the condition of the patient and the magnet system. It is also through the scan room interface circuit 46 that a patient positioning system 48 receives commands to move the patient table to the desired position for the scan.

The gradient waveforms produced by the pulse generator module 38 are applied to gradient amplifier system 42 which is comprised of Gx, Gy and Gz amplifiers. Each gradient amplifier excites a corresponding physical gradient coil in a gradient coil assembly generally designated 50 to produce the magnetic field gradient pulses used for spatially encoding acquired signals. The gradient coil assembly 50 forms part of a magnet assembly 52 that includes a polarizing magnet 54 and a whole-body RF coil 56. A patient or imaging subject 70 may be positioned within a cylindrical imaging volume 72 of the magnet assembly 52. A transceiver module 58 in the system control computer 32 produces pulses that are amplified by an RF amplifier 60 and coupled to the RF coils 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered and digitized in the receiver section of the transceiver 58. The transmit/receive switch 62 is controlled by a signal from the pulse generator module 38 to electrically connect the RF amplifier 60 to the RF coil 56 during the transmit mode and to connect the preamplifier 64 to the coil during the receive mode. The transmit/receive switch 62 can also enable a separate RF coil (for example, a surface coil) to be used in either the transmit or receive mode.

The MR signals sensed by the RF coil 56 are digitized by the transceiver module 58 and transferred to a memory module 66 in the system control computer 32. MRI data is typically collected in a Fourier space known in imaging as "k-space", a reciprocal space connected to real space via a Fourier transform. Each MR signal is encoded with a particular spatial frequency using "phase-encoding" gradient pulses and multiple such MR signals are digitized and stored in k-space for later reconstruction as an image. Typically, frames of data corresponding to MR signals are stored temporarily in the memory module 66 until they are subsequently transformed to create images. An array processor 68 uses a known transformation method, most commonly a Fourier transform, to create images from the MR signals. These images are communicated through the link 34 to the computer system 20 where it is stored in memory, such as disk storage 28. In response to commands received from the operator console 12, this image data may be archived in long term storage, such as on the tape drive 30 or it may be further processed by the image processor 22 and conveyed to the operator console 12 and presented on display 16.

Figure 2:
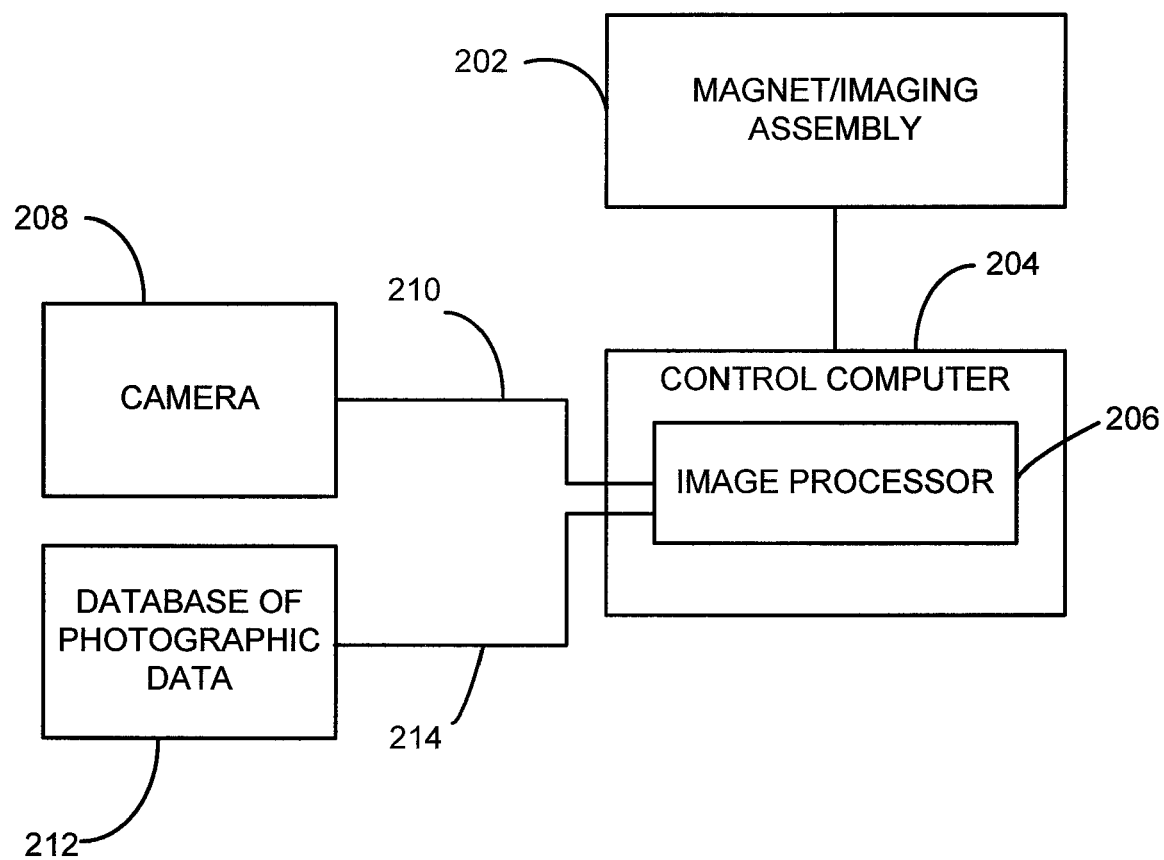
FIG. 2 is a schematic block diagram of an apparatus for generating an image using MRI data and photographic data in accordance with an embodiment.

An apparatus and method for generating images based on MRI data and photographic data may be used with the above-described MR system or any similar or equivalent system for obtaining MR images. FIG. 2 is a schematic block diagram of an apparatus for generating an image using MRI data and photographic data in accordance with an embodiment. A camera 208 is coupled to a control computer 204 of an MRI system, for example, computer 20 or computer 32 of the MRI system 10 (shown in FIG. 1). The control computer 204 is coupled to a magnet/imaging assembly 202 (e.g., magnet assembly 52 shown in FIG. 1) which may include, for example, a magnet (not shown), a gradient coil assembly (not shown), an RF coils(s) (not shown) and an imaging volume (not shown). The camera 208 may be used to obtain photographs (or photographic data) of a patient's anatomy before and/or during and/or after a MRI exam. The photographs or photographic data may be obtained, for example, digitally and the digital photographic data may be communicated to an image processor unit 206 of the control computer 204 using a data communications link 210 which may be, for example, a direct wired communications link or a wireless communications link. Alternatively, control computer 204 and image processor unit 206 may be coupled to a database of photographic data 212 via a communication link 214. Control computer 204 or image processor unit 206 may retrieve photographs or photographic data from database 212 via link 214. The image processor unit 206 may receive MRI data from the control computer 204 or directly from the magnet/imaging assembly 202. The MRI data may be acquired by performing a MR scan of a region of interest in a subject or patient. The image processor unit 206 may include processing capabilities for reconstructing 2-D images from the MRI data and photographic data using image rendering methods such as, for example, volume rendering or surface rendering techniques. In an alternative embodiment, the image processor unit 206 may be replaced by image processing functionality on, for example, a CPU module (not shown) of the control computer 204 or the control computer 204 may communicate with a remote image processing computer (not shown) via an appropriate data communications link (not shown), for example, an internet communications link or a wireless communications link. In an embodiment using a remote image processing computer (not shown), the remote image processing computer may bypass the control computer 204 and communicate directly with the camera 208 or database 212. The resulting 2-D images may be displayed on a display unit, for example, the display 16 of MRI system 10 (shown in FIG. 1) or a remote display (not shown) such as a dedicated display for MRI-guided surgical procedures that may be mounted on the magnet/imaging assembly 202, on a scan-room wall, or may be located in another room.

Figure 3:
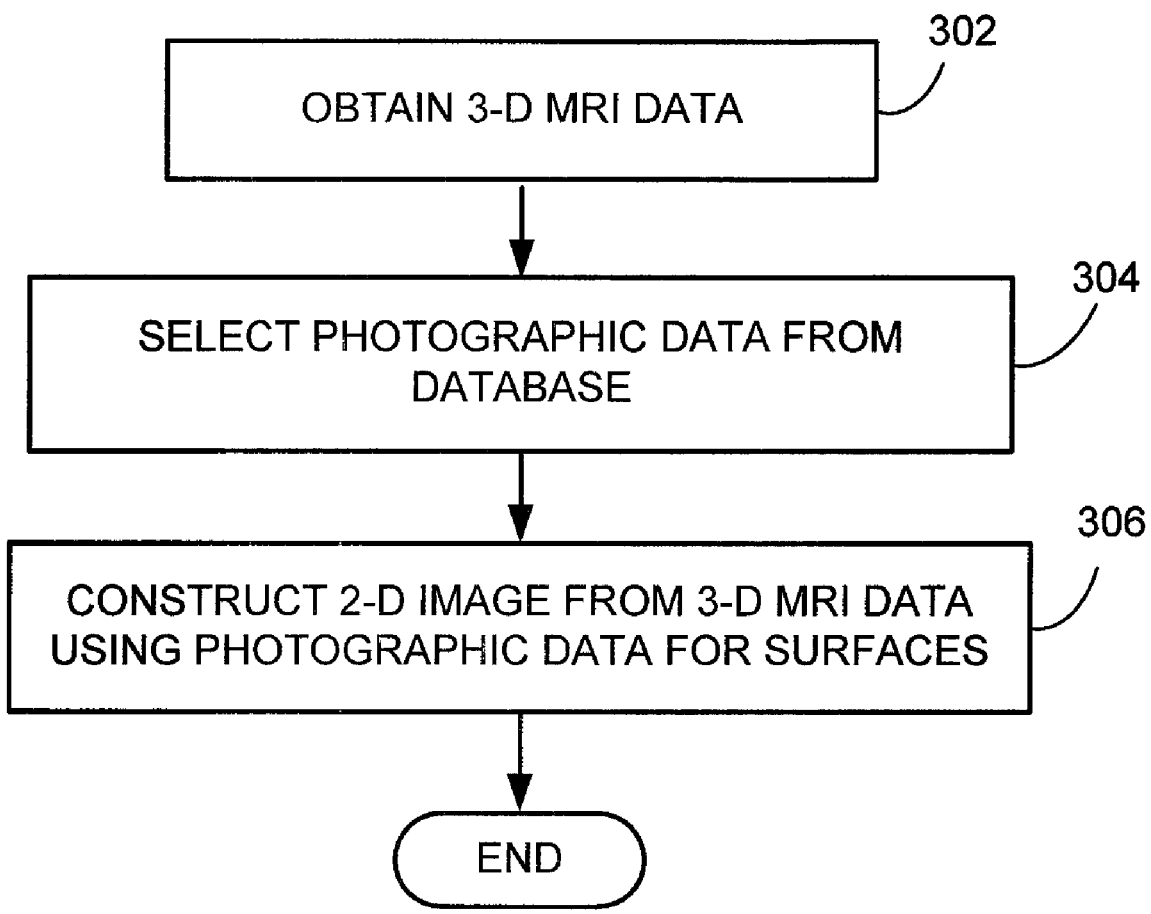
FIG. 3 is a flowchart of a method for generating an image using photographic data to depict surfaces in a 2-D image of MRI data in accordance with an embodiment.

FIG. 3 is a flowchart of a method for generating an image using photographic data to depict surfaces in a 2-D image of MRI data in accordance with an embodiment. At block 302, MRI data is obtained for a region of interest in a subject or a patient. MRI data may be acquired using a MRI scanner such as the exemplary MRI scanner described in FIG. 1. Alternatively, MRI data may be acquired from a database of stored MRI data or retrieved from a storage medium such as a compact disc (CD) or a digital versatile disk (DVD). At block 304, photographic data is selected from a database of photographic data (e.g., database 212 shown in FIG. 2). An entire photograph, or portions thereof, may be selected from the database by a user or may be selected automatically based on input from a user (e.g., the photographic data may be automatically selected by a control computer 204 shown in FIG. 2). A user may select a photograph that best matches a patient's physical characteristics by visually inspecting photographs belonging to the database of photographs. For example, for an MRI data-set corresponding to a patient's head, a user may select a photograph of a face/head on the basis of the similarity of appearance of the face/head to the patient. Alternatively, a user may enter information about a patient's physical characteristics, such as skin color, sex, age, etc. and a photograph may be automatically selected from the database on the basis of these characteristics.

The selected photographic data may be used to create a more realistic-looking 2-D image generated from the MRI data using an image rendering method. At block 306, a 2-D image of the patient's anatomy is created or constructed using an image rendering method using photographic data from block 304 to depict surfaces and using a 3D MRI data-set acquired at block 302 to depict underlying structures. Examples of image rendering methods include surface-rendering techniques and volume-rendering techniques. Surface-rendering techniques may include generating models of surfaces using polygonal mesh surfaces, such as by using a "marching cubes" algorithm, or based on spline representations such as a Nonuniform Rational Basis Spline (NURBS). Photographic data from block 304 may be mapped directly onto a surface in the 2-D image. Alternatively, attributes of the photographic data may be used to derive input parameters for the image rendering method. For example, a photograph of a person's face selected at block 304 may be analyzed automatically (e.g., using an image processor such as image processor 206 shown in FIG. 2) to determine an average skin color for the person's face. The skin color may then be used by the image rendering method to depict all surfaces that correspond to skin in the resultant 2-D image. In another example, a selected photograph of a person's face may be analyzed automatically to determine values for the distance between the person's eyes, the height of their nose, their lip color, and other attributes which may be used by the image rendering method to more realistically render a person's face on the corresponding surface. As another example, a photograph selected at block 304 may be analyzed automatically and used to select or to generate a texture map that may be mapped onto a surface. A set of texture maps may be stored in a library or database and the photographic data may be compared with the texture maps in the library to select which texture map to use in rendering the surface. Alternatively, a patient-specific texture map may be generated using a set of parameters derived automatically from the photographic data. A texture map may be derived using, for example, procedural modeling or by altering the average color of a stored texture map.

Figure 4:
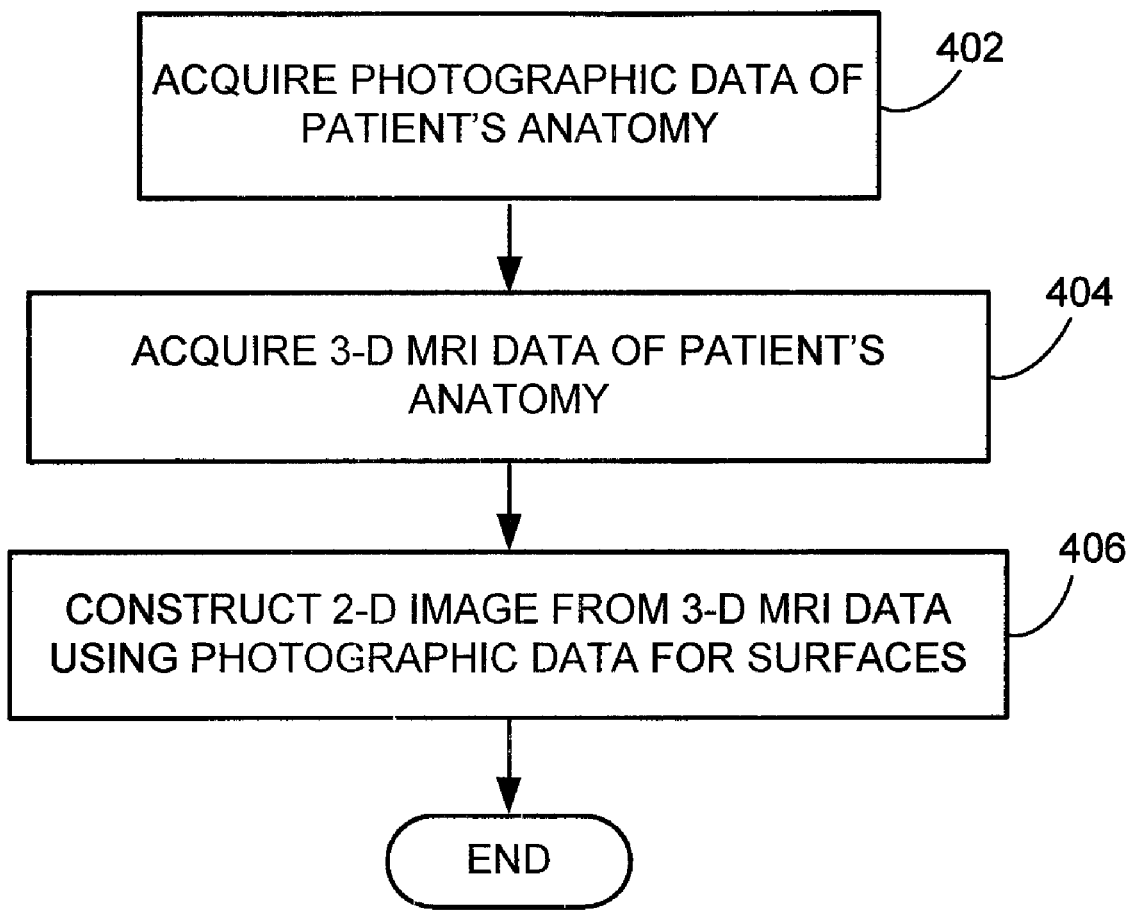
FIG. 4 is a flowchart of a method for generating an image using photographic data and MRI data in accordance with an embodiment.

In an alternative embodiment, photographic data for the same patient or subject scanned using MRI may be acquired and used to generate a 2-D image from the 3-D MRI data. FIG. 4 is a flowchart of a method for generating an image using photographic data and MRI data in accordance with an embodiment. At block 402, photographic data is acquired or obtained of a patient's anatomy, for example, for a particular region of interest. The photographic data may be obtained prior to an MRI exam or during an MRI scanning exam by using cameras (e.g., camera 208 shown in FIG. 2) arranged near the MRI scanner. For MRI-guided surgical procedures, the cameras may be arranged inside of the scanner or near its opening to facilitate taking photographs at multiple time-points during the surgical procedure. The method shown in FIG. 4 may be carried out at multiple time-points during the procedure. The photographic data may capture information about the patient's external surfaces or it may capture information about the surfaces of internal organs or tissues when exposed during a surgical procedure.

For MRI-assisted endoscopic procedures, a camera may be arranged to obtain photographs of surfaces interior to the patient using, for example, an optical fibre wave-guide. One example of a MRI-assisted endoscopic procedure is a colonoscopy. During a colonoscopy, photographic images of the interior walls of the colon may be obtained. At block 404, 3-D MRI data of the patient's anatomy may be acquired using an MRI system such as is described above with respect to FIG. 1. At block 406, a 2-D image of the patient's anatomy may be created or constructed using an image rendering method (as described above with respect to FIG. 3) with photographic data acquired at block 402 used to depict surfaces and a 3-D MRI data-set acquired at block 404 used to depict underlying structures.

For MRI-guided surgical procedures, the 2-D images may be used to display theoretical or actual trajectories of surgical instruments relative to the patient's anatomy. For example, an operator of a surgical instrument (e.g., a surgeon, or an interventional radiologist) may hold the instrument at varying angles to a patient's head at a possible entry point to the skull. As the instrument is moved, the 2-D images may be updated to show theoretical approaches into the brain based on the position and orientation of the instrument. In this way, a surgical approach to a target location inside the brain may be planned with reference both to the internal structures depicted using the MRI data and the surface data depicted using the photographic data.

Computer-executable instructions for using an image rendering method to render an MR image using 3-D MRI data and 2-D photographic data according to the above-described method may be stored on a form of computer readable media. Computer readable media includes volatile and nonvolatile, removable and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and may be accessed by any method including by internet or other computer network forms of access.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

I claim:

1. A method for generating an image of a region of interest of a subject, the method comprising:

obtaining a set of magnetic resonance (MR) data for the region of interest;

obtaining photographic data for at least one surface of the region of interest; and generating an image using the set of MR data to generate a depiction of at least one structure of the region of interest and using the photographic data to generate on the image a depiction of at least one surface of the region of interest.

2. A method according to claim 1, wherein generating an image comprises using a volume rendering technique.

3. A method according to claim 1, wherein generating an image comprises using a surface rendering technique.

4. A method according to claim 1, wherein obtaining a set of MR data for the region of interest comprises performing an MR scan of the region of interest.

5. A method according to claim 1, wherein obtaining a set of MR data for the region of interest comprises selecting a set of MR data from a database.

6. A method according to claim 1, wherein obtaining photographic data for at least one surface of the region of interest comprises selecting the photographic data from a database.

7. A method according to claim 1, wherein obtaining photographic data for at least one surface of the region of interest comprises photographing the region of interest.

8. A method according to claim 1, wherein a set of surface attributes for the at least one surface is based on the photographic data.

9. A method according to claim 1, wherein using the photographic data to generate a depiction of at least one surface of the region of interest comprises selecting a texture map for the at least one surface based on the photographic data.

10. A method according to claim 9, wherein selecting a texture map comprises comparing the photographic data to a plurality of texture maps in a database.

11. A method according to claim 1, wherein using the photographic data to generate a depiction of at least one surface of the region of interest comprises deriving a texture map based on the photographic data.

12. A non-transitory computer readable medium having computer executable instructions for performing a method for generating an image of a region of interest of a subject, the computer readable medium comprising:

program code for receiving a set of magnetic resonance (MR) data for the region of interest;

program code for receiving photographic data for at least one surface of the region of interest; and program code for generating an image using the set of MR data to generate a depiction of at least one structure of the region of interest and using the photographic data to generate on the image a depiction of at least one surface of the region of interest.

13. A non-transitory computer readable medium according to claim 12, wherein the program code for generating an image comprises a volume rendering-technique.

14. A non-transitory computer readable medium according to claim 12, wherein the program code for generating an image comprises a surface rendering technique.

15. A non-transitory computer readable medium according to claim 12, wherein the program code for generating an image comprises program code for selecting a texture map for the at least one surface of the region of interest based on the photographic data.

16. A non-transitory computer readable medium according to claim 15 wherein the program code for selecting a texture map comprises program code for comparing the photographic data to a plurality of texture maps in a database.

17. A non-transitory computer readable medium according to claim 12, wherein the program code for generating an image comprises program code for deriving a texture map based on the photographic data.

18. An apparatus for generating an image of a region of interest of a subject, the apparatus comprising:
- a camera configured to obtain photographic data for at least one surface of the region of interest;
- a magnetic resonance imaging assembly configured to obtain a set of magnetic resonance (MR) data for the region of interest; and
- an image processor coupled to the camera and the magnetic resonance imaging assembly, the image processor configured to generate an image using the set of MR data to generate a depiction of at least one structure of the region of interest and using the photographic data to generate on the image a depiction of at least one surface of the region of interest.

19. An apparatus for generating an image of a region of interest of a subject, the apparatus comprising:
- a database comprising photographic data;
- a magnetic resonance imaging assembly configured to obtain a set of magnetic resonance (MR) data for the region of interest; and
- an image processor coupled to the database and the magnetic resonance imaging assembly, the image processor configured to generate an image using the set of MR data to generate a depiction of at least one structure of the region of interest and using a selected set of photographic data from the database to generate on the image a depiction of at least one surface of the region of interest.

20. A method according to claim 1, wherein obtaining the photographic data comprises capturing image information for the region of interest during an imaging exam using a camera.

21. A method according to claim 1, wherein obtaining the photographic data comprises capturing image information for an external surface of a patient including the region of interest.

22. A method according to claim 1, wherein obtaining the photographic data comprises capturing image information for a surface of one of an internal organ or tissue of a patient including the region of interest.

23. A method according to claim 1, wherein generating the image comprises generating a two-dimensional image from the MR data with an increased realistic look using the photographic data.

* * * * *